United States Patent [19]
Holland, Jr. et al.

[11] Patent Number: 6,053,886
[45] Date of Patent: Apr. 25, 2000

[54] SWITCH APPARATUS FOR OPERATING AN EVACUATOR

[75] Inventors: Clinton R. Holland, Jr.; Earnest R. Moehlau, both of Amherst; Christopher A. Palmerton, Clarence; Charles T. Taverner, Amherst, all of N.Y.

[73] Assignee: Medtek Devices, Inc., Amherst, N.Y.

[21] Appl. No.: 08/909,902

[22] Filed: Aug. 12, 1997

[51] Int. Cl.[7] .................................................. A61N 1/30
[52] U.S. Cl. .............................. 604/22; 604/67; 604/118; 606/10
[58] Field of Search ................................ 604/22, 118, 65, 604/67, 31; 606/10

[56] References Cited

U.S. PATENT DOCUMENTS

| | | |
|---|---|---|
| 4,740,202 | 4/1988 | Stacey et al. . |
| 5,108,389 | 4/1992 | Cosmescu . |
| 5,318,516 | 6/1994 | Cosmescu . |
| 5,520,633 | 5/1996 | Costin . |
| 5,620,441 | 4/1997 | Greff et al. . |
| 5,626,560 | 5/1997 | Soring . |

*Primary Examiner*—Mark Bockelman
*Attorney, Agent, or Firm*—Phillips, Lytle, Hitchcock, Blaine & Huber LLP

[57] ABSTRACT

The current invention is directed to a switch apparatus (6) for operating a surgical evacuator (14). The switch apparatus broadly comprises a surgical device (39) having a power unit (12), a vibration generator (10) for producing vibrations in response to the operation of the surgical device, a vibration sensor (22) for generating an output as a function of vibrations sensed, a control unit (23) for producing a control signal as a function of the vibrations produced by the vibration generator and a surgical evacuator for removing a waste product generated by the use of the surgical device. The vibration generator is adaptively coupled to the power unit. In addition, the control unit is adaptively coupled to the vibration sensor. The evacuator is responsive to the control signal and is activated or deactivated based on the operation of the surgical device. In one embodiment, the control unit is comprised of an amplifying means (34), a filter means (47), a frequency sensor means (37), a first delay circuit (38), a second delay circuit (40) and an output circuit (42). The amplifier means amplifies output from the vibration sensor and the frequency sensor means detects the frequencies generated by the vibration generator and produces a control signal in response to such detection. The control signal then turns the evacuator on or off.

4 Claims, 5 Drawing Sheets

SWITCH APPARATUS FOR OPERATING AN EVACUATOR

TECHNICAL FIELD

The present invention relates generally to the field of surgical evacuators, and more particularly, to a switch apparatus for automatically controlling a surgical evacuator in response to the operation of a surgical device, such as an electrosurgical unit, a surgical laser, or a surgical power tool.

BACKGROUND ART

The use of surgical devices is quite common in many modern surgical procedures. Such devices assist surgeons in performing operations that were previously difficult or impossible to perform. However, many surgical devices, such as surgical lasers, electrosurgical units (ESU's), ultrasonic units, surgical drills, surgical power tools, endoscopic and laparoscopic tools, tools for use in open procedures, and any other tool to assist a surgeon in minimal evasive and evasive procedures, generate waste products during use.

In the case of surgical saws, drills and the like, the waste product generated consists of blood, bone chips, smoke and other particulate matter which may contain viruses, bacteria and other noxious and toxic substances capable of transmitting disease. In the case of ESU's and surgical lasers, the primary waste product is in the form of a smoke plume.

Health concerns raise a significant reason to remove smoke plumes. It is known that smoke plumes can carry active particles such as viruses, bacteria mycobacteria and other microbes or toxins. Additionally, chemical mixes used in medical procedures can generate hazardous vapors also found in smoke plumes. The particles and vapors found in a smoke plume may be transmitted to the staff performing the medical procedure, or the patient undergoing surgery, through contact with the plume. Furthermore, these particles and vapors can remain suspended in the operating room, thus exposing the next patient or surgical staff.

Government agencies have recently begun to investigate smoke plumes and now advise the removal or filtering of smoke plumes generated by laser surgery. See "OSHA Technical Manual—Section V—Chapter 1 Appendix V:1–3, Physical Agents", "OSHA Technical Manual—Section V—Chapter 1, Hospital Investigations: Health Hazards" and "Health Hazard Information Bulletin: Hazards of Laser Surgery Smoke", Apr. 11, 1988. This concern has extended to other procedures generating smoke plumes such as electrosurgery. See "Standard Interpretations and Compliance Letters—Hazards of Smoke Generated from Surgical Procedures" at http://www.osha-slc.gov. Furthermore, the "1996 Standard & Recommended Practices" issued by the Association of Operation Room Nurses, Inc. recommends removal of smoke plumes during electrosurgical procedures, and the Center for Disease Control and Prevention (CDC) and the National Institute for Occupational Safety and Health (NIOSH) issued in September of 1996 issued a Hazard Control II (HCII) entitled "Control of Smoke from Laser/Electric Surgical Procedures" similarly recommending removal of smoke plumes generated by electrosurgery.

Accordingly, it is desirable to have a system in place near the site of the surgery to remove such waste products before they come in contact with surgeons, nurses and other medical staff in near proximity to the surgery. This area is often called the "breathing zone". The most common system for waste removal is the surgical evacuator. The evacuator removes waste product by generating a partial vacuum in the vicinity of the site of the surgical procedure. Air, gas, liquid or other fluid containing the waste product is drawn through the evacuator, filtered to acceptable levels and vented.

In the past, various methods have been used to control the operation of evacuators. Early forms of control were direct manual operation of the evacuator. In this method, the surgical procedure was monitored continually by a member of the surgical staff. The surgical evacuator would be manually activated by the staff member upon commencement of the surgical procedure, and then manually deactivated at the termination of the surgical procedure. This system presented several problems. Typically it required the services of a staff member other than the surgeon, as the surgeon was preoccupied with performing the surgery at hand. In certain circumstances, members of the surgical staff would not remember to activate or deactivate the evacuator at the appropriate times. Thus, situations sometimes arose where smoke plumes generated by the surgical procedure were not removed through evacuation. Other situations would arise where the evacuator, although activated at the commencement of the surgery, was not deactivated at the termination of the surgery. This resulted in additional and unnecessary operation of the evacuator, thus reducing the effective life of filters implemented in the evacuator, along with increased wear and tear on particular components in the evacuator.

As a result, attempts have been made to solve such problems. In U.S. Pat. No. 5,108,389, a smoke evacuator system is disclosed in which a foot switch is provided. The switch is coupled to a smoke evacuator, such that operation of the foot switch by a surgeon causes the smoke evacuator to activate or deactivate. This invention, however, still requires conscious monitoring by the surgical staff. The surgeon or staff member must remember to operate the foot switch at the appropriate time to either turn the evacuator on or off. In addition, inadvertent movement by a member of the staff could cause the switch to accidentally activate or deactivate the evacuator at inopportune times during the surgical procedure. Hence, it is desirable to provide an automatic method of controlling the evacuator such that the evacuator is turned on contemporaneously with commencement of use of a surgical device, and turned off at approximately the same time that the surgical device is turned off.

One apparatus for providing automatic control of an evacuator is disclosed in U.S. Pat. No. 5,318,516. The '516 patent discloses an apparatus using a radio frequency (RF) sensor for automatic control of a smoke evacuator. The sensor detects stray RF energy emitted by the operation of the power supply of an ESU or surgical laser and activates an evacuator in response. Although this reference teaches use of an RF sensor to detect the operation of a surgical laser or ESU, it is desirable to develop a control apparatus which operates on other principles.

The presence of RF energy is very undesirable in an operating room. RF energy interferes with the operation of many other medical instruments which rely on electronic signals. The operation of devices such as pacemakers, monitoring units, and other sensitive pieces of electronic medical equipment may be disrupted by the presence of stray RF energy in the operating room. Hence, a movement is underway to develop operating rooms which minimize the presence of RF energy. Requirements for RF shielding on medical devices, and limitations on RF energy are now being implemented in various countries. Accordingly, it is very desirable to develop an apparatus that automatically controls the operation of an evacuator in the absence of RF energy.

U.S. Pat. No. 5,620,441 also discloses a remote switch apparatus for the automatic control of a smoke evacuator.

This invention relies on the electrical characteristics of a conductor connected to a surgical device to automatically control an evacuator. The system of the '441 patent requires that a specialized inductive sensor be placed in immediate proximity to the conductor which connects the power supply and the hand piece of an electrosurgical unit (ESU). When power is provided to the handpiece, a high frequency electrical current passes from the power unit of the ESU through the conductor and induces a current flow in the inductive sensor, which in turn actuates the evacuator.

Because the inductive sensor of the '441 patent relies on a transformer to induce high frequency currents within a secondary winding, it may generate undesirable EMF within the operating room. For the reasons stated above, it is desirable to develop a switching apparatus which does not rely on either RF or high frequency electrical signals for activation and deactivation of an evacuator.

DISCLOSURE OF THE INVENTION

With parenthetical reference to the corresponding parts, portions or surfaces of the disclosed embodiment, merely for purposes of illustration, and not by way of limitation, the present invention broadly provides an improved switch apparatus (6) for operating a surgical evacuator (14). The switch apparatus broadly comprises a surgical device (39) having a power unit (12), a vibration generator (10) for producing vibrations in response to the operation of the surgical device, a vibration sensor (22) for sensing vibrations and for generating an output as a function of the vibrations sensed, a control means (23) and a surgical evacuator. The vibration generator is adaptively coupled to the power unit. The control means is adaptively coupled to the vibration sensor, and produces a control signal as a function of the vibrations produced by the vibration generator. The surgical evacuator is used to remove the waste product generated by the use of the surgical device and is responsive to the control signal.

The control means comprises an amplifier means (34) for amplifying the output from the vibration sensor and a switching means (32) for generating the control signal. A filter means (47) is also provided, and is arranged in cooperative relationship with the amplifier means to filter extraneous frequencies. The switching means is arranged in cooperative relationship with the amplifier means. The switching means further comprises a frequency sensor means (37) and a first delay circuit (38). The frequency sensor detects particular frequencies produced by the vibration generator and generates a control signal in response to the detection of any of such particular frequencies. The first delay circuit delays the recognition of the particular frequencies.

A second delay circuit (40) is arranged in cooperative relationship with the switching means to delay transmission of the control signal to the evacuator. In this manner, the evacuator may be selectively energized with respect to the operation of the surgical device.

In one embodiment, the vibration generator produces vibrations at a first frequency in response to a first operating state of the surgical device, and produces vibrations at a second frequency in response to a second operating state of the surgical device. Here, the frequency sensor means may comprise a first frequency decoder (44) and a second frequency decoder (45). Each of these decoders are adjustable such that the first decoder produces the control signal in response to sensing the first frequency and the second frequency decoder produces the control signal in response to sensing the second frequency.

In an alternate embodiment, the control means comprises a microprocessor (60) having a plurality of storage registers (61). A frequency sensor means (62) for detecting particular frequencies is arranged in cooperative relationship with the microprocessor such that the microprocessor will store a particular frequency in one of the storage registers after such frequency has been sensed for a predetermined period of time. The frequency sensor means and microprocessor then operate in functional cooperation to detect any of the particular frequencies stored in the plurality of registers and the microprocessor generates the control signal in response to detecting such frequencies.

The surgical device may take many forms including an electrosurgical unit, a surgical laser, or a surgical power tool.

The surgical device may have a power unit (12). The vibration generator may be coupled to the power unit. The power unit has an exterior portion (28) so configured and arranged that operation of the vibration generator causes the exterior portion to vibrate. The vibration sensor and control means are provided within a housing assembly (29) mounted to the exterior portion of the power unit. The housing assembly comprises an enclosure (21) and a base (25). The base is disposed between the exterior portion of the power unit and the enclosure such that vibrations transmitted to the vibration sensor are attenuated. The base is comprised of a resilient material such as a ethylene propylene diene monomer (EPDM). The exterior portion of the power unit may have a plurality of transmission slots (9). The housing assembly can be mounted in proximity to these slots.

The surgical evacuator is controlled in the following manner. First, the surgical device is operated. In turn, vibrations are generated by the vibration generator in response to the operation of the surgical device. The vibration sensor senses such vibrations and generates an output as a function of the vibrations. The control means then generates a control signal as a function of the output of the vibration sensor by amplifying such output and performing a switching operation upon detection of a particular frequency. In addition, the control means also filters the output from the vibration sensor and delays transmission of the control signal to the evacuator. The surgical evacuator then is either activated or deactivated in response to the control signal.

Accordingly the general object of the present invention is to provide an improved switch apparatus for operating an evacuator.

Another object of the present invention is to provide an improved switch apparatus for operating an evacuator which is capable of actuating the evacuator automatically based on the frequencies of the vibrations generated by a speaker present in the power unit of a surgical device.

Another object of the present invention is to provide an improved switch apparatus which is resiliently mounted on the power supply for a surgical device and which is located at optimal points of vibration on such power supply.

Another object of the present invention is to provide an improved switch apparatus which may be readily transferred between different power supplies, which is readily modifiable, economical to manufacturer, reliable, rugged, and may be used with a variety of surgical devices.

Another object of the present invention is to provide an improved switch apparatus which may be adjusted to detect a number of different vibrational frequencies.

Another object of the present invention is to provide an improved switch apparatus which may be automatically tuned to detect a number of different vibrational frequencies.

These and other objects and advantages will become apparent from the foregoing and ongoing written specification, the drawings and the appended claims.

DESCRIPTION OF THE PREFERRED EMBODIMENTS

Figure 1:
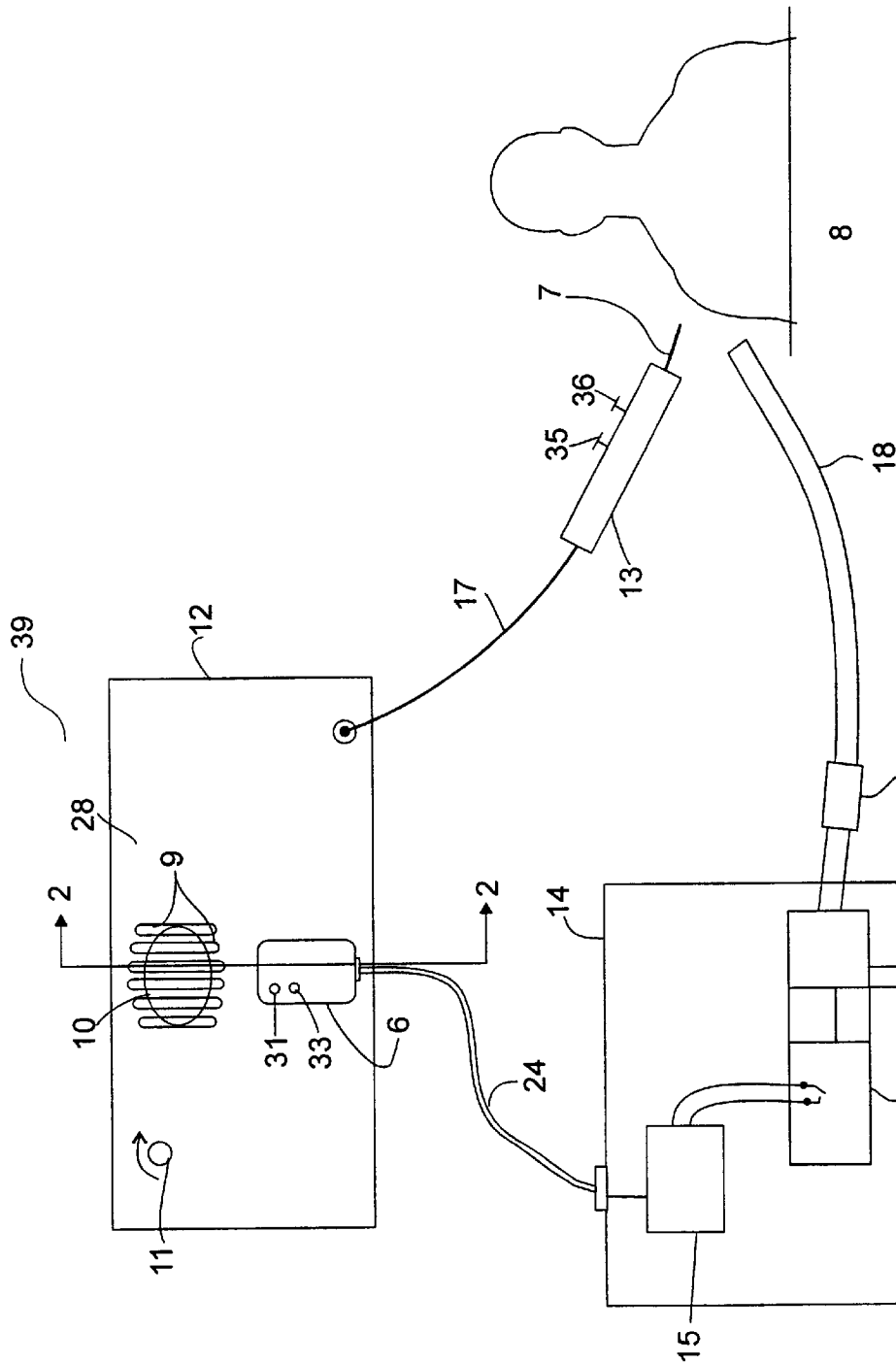
FIG. 1 is a schematic view, showing the improved switch apparatus as set forth in the present invention, an evacuator, and an electrosurgical unit.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

The present invention is particularly intended to provide an improved apparatus for selectively energizing a surgical evacuator. Referring now to the drawings, and more particularly to FIG. 1 thereof, this invention provides an improved switch apparatus, indicated generally at 6. A surgical device 39 is provided, and is depicted as an electrosurgical unit (ESU) in the present embodiment. Electrosurgical unit 39 is broadly comprised of a power unit 12, an electrosurgical unit pen 13 (ESU pen), and a conductor 17. ESU pen 13 is connected to power unit 12 via conductor 17. It is noted that surgical device 39 could just as well be a surgical laser or a surgical drill. Switch apparatus 6 is shown as being mounted to an exterior portion (28) of power unit 12.

ESU pen 13 contains a cutting tip 7 which, through the transmission of energy from power unit 12, causes either cutting or coagulation of tissue at a surgical site 8. Typically, surgical site 8 represents a person or animal undergoing a surgical procedure. Electrosurgical pen 13 contains two activation buttons 35, 36. Depression of button 35 causes tip 7 to perform a cutting operation through use of high frequency current flowing from power unit 12. Depression of button 36, in a similar fashion, causes a coagulation operation to be performed. Coagulation mode requires a different current flow from power unit 12 and is used when surgery requires that the flow of blood be reduced or stopped at the surgical site.

In addition to causing either cutting or coagulation operations, depression of buttons 35, 36 also cause activation of a vibration generator, depicted as a speaker 10. Speaker 10 is located within power unit 12. Depression of button 35 causes speaker 10 to emit an audible warning sound at a first frequency. Depression of button 36 causes speaker 10 to emit an audible warning sound at a second, different frequency. The volume of these warning sounds may be adjusted with volume control knob 11. The activation of speaker 10 occurs automatically upon depression of either of buttons 35, 36. This is done for safety purposes so that the members of a surgical team present in a surgical room are made aware of when ESU pen 13 is in operation. Thus, when members of the surgical staff hear a first tone, they are warned that the ESU pen 13 is set in cut mode; when they hear a second tone, they are warned that ESU pen 13 is set in coagulation mode. This reduces the opportunity for accidental injury from ESU pen 13.

At the time either a cutting or a coagulation operation is performed, a smoke plume (not shown) is generated containing various noxious substances. Switch apparatus 6 actuates a smoke evacuator 14 to remove such waste products at the time either of buttons 35, 36 are depressed. Upon release of either of buttons 35, 36, vibrations cease and switch apparatus 6 turns evacuator 14 off to save energy, increase filter life, and reduce wear on internal components of evacuator 14.

Power unit 12 is provided with an exterior portion 28 having an outer surface. A plurality of elongated parallel transmission slots, severally indicated at 9 are provided within exterior portion 28. Slots 9 provide for the adequate transmission of sound from speaker 10 to warn the surgical staff of the operation of ESU pen 13. Operation of speaker 10 causes mechanical vibrations to be induced throughout power unit 12, including exterior portion 28 of power unit 12. The amplitude of these vibrations will vary depending on the type of power unit in use, and the setting of volume control knob 11.

Switch apparatus 6 is mounted on the outer surface of power unit 12 in proximity to transmission slots 9. As seen more fully in FIG. 2, switch apparatus 6 is comprised of a vibration sensor 22 and a control means 23. Control means 23 is depicted as being a control unit in the form an electronic circuit board assembly. Switch apparatus 6 communicates with evacuator 14 by way of a cable 24. Adverting to FIG. 1, cable 24 plugs into evacuator 14 by means of a removable plug (not shown). Evacuator 14 is comprised of a microprocessor unit 15, a vacuum pump assembly 16, a suction tube 18, an in-line filter 19, and a vent port 20. Activation of vacuum pump assembly 16 is controlled by microprocessor 15. In typical operation, evacuator 14 is used to remove the smoke or other debris generated by ESU pen 13 during a surgical procedure. Smoke and other debris are drawn by vacuum pump 16 through suction tube 18, filtered by in-line filter 19 and vented through vent port 20.

The system operates as follows. The practitioner performing a surgical procedure depresses either buttons 35, 36 to begin operating at surgical site 8. At that time, speaker 10 is activated by the internal circuitry of power unit 12. Speaker 10 emits a warning tone, and generates mechanical vibrations within the exterior portion 28 of power unit 12. Vibration sensor 22 detects such vibrations and provides an output to control means 23. Control means 23 then provides a control signal via cable 24 to microprocessor 15 of evacuator 14. Upon receiving the control signal, microprocessor 15 directs vacuum pump assembly 16 to energize. Vacuum pump assembly 16 creates a vacuum at the end of flexible suction tube 18 to remove any smoke or other debris generated by the operation of ESU pen 13.

When the surgeon releases either button 35 or 36, speaker 10 no longer emits an audible tone and the mechanical vibrations in the exterior portion 28 of power unit 12 cease. Sensor 22 no longer senses the vibrations in the exterior portion of power unit 12 and control means 23 transmits a control signal to microprocessor 15 directing that vacuum pump assembly 16 be turned off. Upon deactivation of the vacuum pump assembly, a vacuum is no longer draw at the surgical site.

In this manner, evacuator 14 operates in functional relationship with electrosurgical unit 39. When electrosurgical unit 39 is in operation, evacuator 14 is in operation. When electrosurgical unit 39 is no longer in operation, evacuator 14 ceases to operate. This is desirable because evacuator 14 is kept in operation only during that period of time necessary to evacuate harmful smoke generated by the surgical procedure.

As stated earlier, depression of either of buttons 35, 36 will cause speaker 10 to emit a tone at either a first frequency or second frequency. As seen in FIG. 1, switch apparatus 6 is provided with adjustable potentiometers 31, 33 which allow switch apparatus 6 to be tuned to detect those particular frequencies generated by speaker 10. The initial adjustment of potentiometers 31, 33 is initially performed as a setup operation prior to use of switch apparatus 6. Potentiometers 31, 33 must be adjusted so that a control signal is generated to activate evacuator 14 in response to the vibrations generated by speaker 10, but not in response to extraneous vibrations caused by dropped objects or other vibration sources. To perform the appropriate adjustment of potentiometers 31, 33, the volume of speaker 10 is first adjusted to its midpoint value by operation of volume control knob 11. Button 35 of ESU pen 13 is then held in its depressed position so that speaker 10 emits a tone at a first frequency and potentiometer 33 is rotated in a counterclockwise direction until evacuator 14 turns on. Rotation of potentiometer 33 is continued until evacuator 14 turns off. Potentiometer 33 is then positioned at approximately the midpoint between the on and off settings determined above. This provides the most accurate adjustment of potentiometer 33 with respect to the frequency generated by speaker 10 when button 35 is depressed. Potentiometer 31 is then adjusted in a similar fashion, except it is tuned to correspond to the frequency emitted by the depression of button 36.

Switch apparatus 6 may be removed from the exterior portion of power unit 12 and placed on different power units. At such time, readjustment of potentiometers 31, 33 may be required if the speaker associated with such new power unit emits different frequencies corresponding to the depression of buttons 35, 36.

In operation, switch apparatus 6 receives power via cable 24 from the power supply of evacuator 14. Hence, cable 24 serves a two-fold purpose: during operation it provides power to switch apparatus 6 and also returns a control signal to cause activation or deactivation of evacuator 14.

Figure 2:
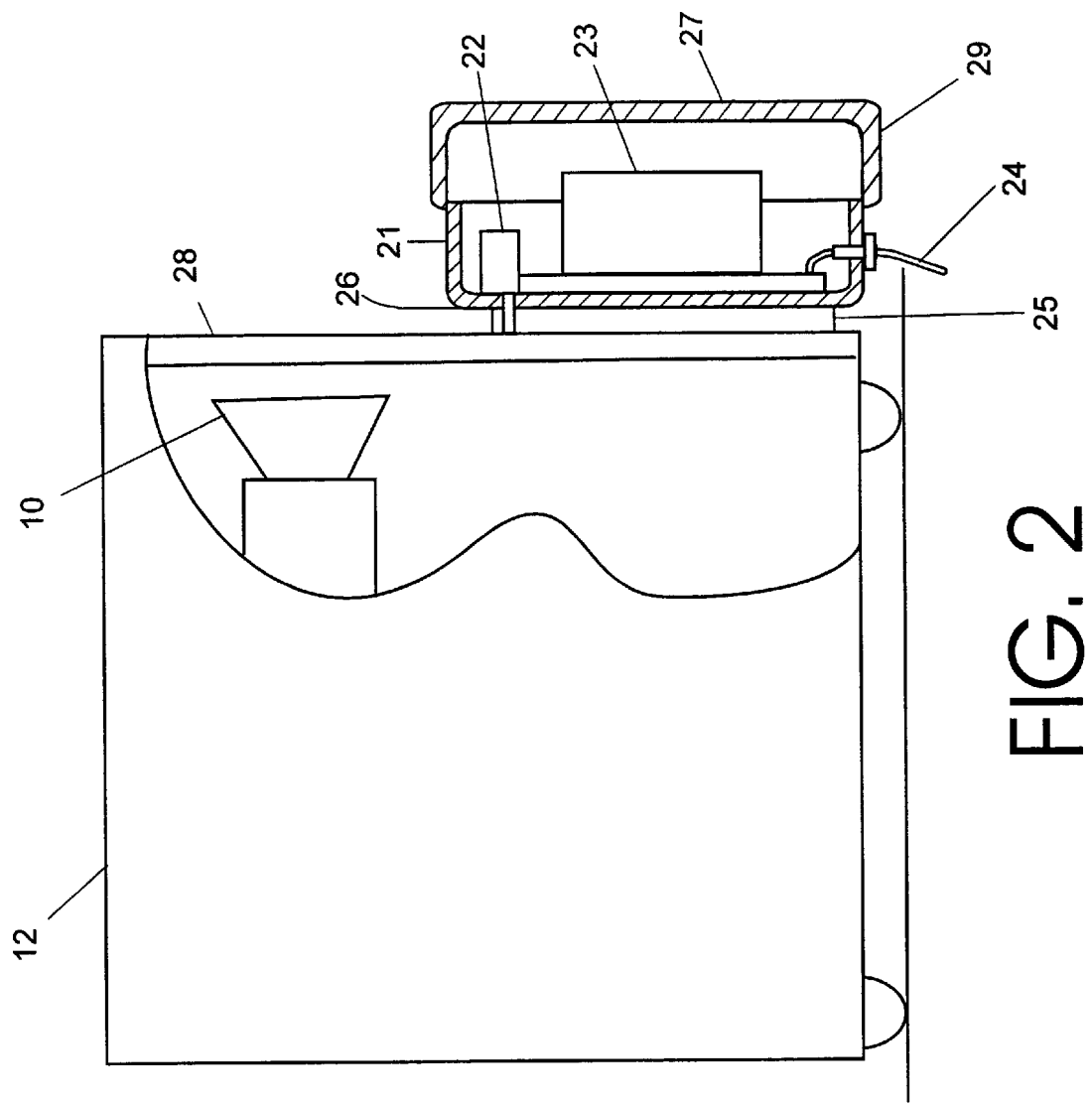
FIG. 2 is a fragmentary vertical view, partly in section and partly in elevation, of the improved switch apparatus and the power supply of the surgical apparatus, taken along the view line 2—2 of FIG. 1.

FIG. 2 depicts a detailed view of switch apparatus 6 mounted to exterior portion 28 of power unit 12. Switch apparatus 6 is comprised of a housing assembly 29 and cable 24. Housing assembly 29 is comprised of a rectangular cup-shaped enclosure 21, a rectangular cup-shaped cover 27 and a base 25. Enclosure 21 and cover 27 are comprised of a thermoplastic material and are configured and arranged to completely enclose sensor 22 and control unit 23 from the elements.

Vibration sensor 22 may consist of any number of transducers capable of detecting mechanical vibrations. Hence, sensor 22 may include accelerometers, pressure transducers, and microphones. Control unit 23 is in the form of a circuit board assembly which is fixedly mounted to the bottom portion of enclosure 21. This is accomplished through the use of adhesive bonding agent such as a glue or epoxy.

Base 25 is mounted to the outer surface of exterior portion 28 of power unit 12, and is disposed between enclosure 21 and power unit 12. Base 25 is preferably comprised of a resilient material, such as an ethylene propylene diene monomer (EPDM). This material possesses resilient qualities and is used to attenuate the vibrations generated from exterior portion 28 from transmission into switch apparatus 6. Base 25 is a thin rectangular-shaped element provided with an adhesive material on both of its outer surfaces. In this manner, base 25 is adhered to the outer surface of power unit 12 and is adhered to enclosure 21 at interface 26. The thickness of base 25 is critical for proper operation of switch apparatus 6. In the situations where base 25 is too thin, or is not used at all, switch apparatus 6 may be overly sensitive. In this situation, switch apparatus 6 may accidentally activate evacuator 14 in response to extraneous vibrations other than vibrations caused by speaker 10. It has been determined that the optimal thickness of base 25 is approximately 0.125 inches for proper attenuation and transmission of vibrations. Thicknesses substantially greater than 0.125 inches cause switch apparatus 6 to fail to activate evacuator 14 in response to the vibrations caused by speaker 10.

Figure 3:
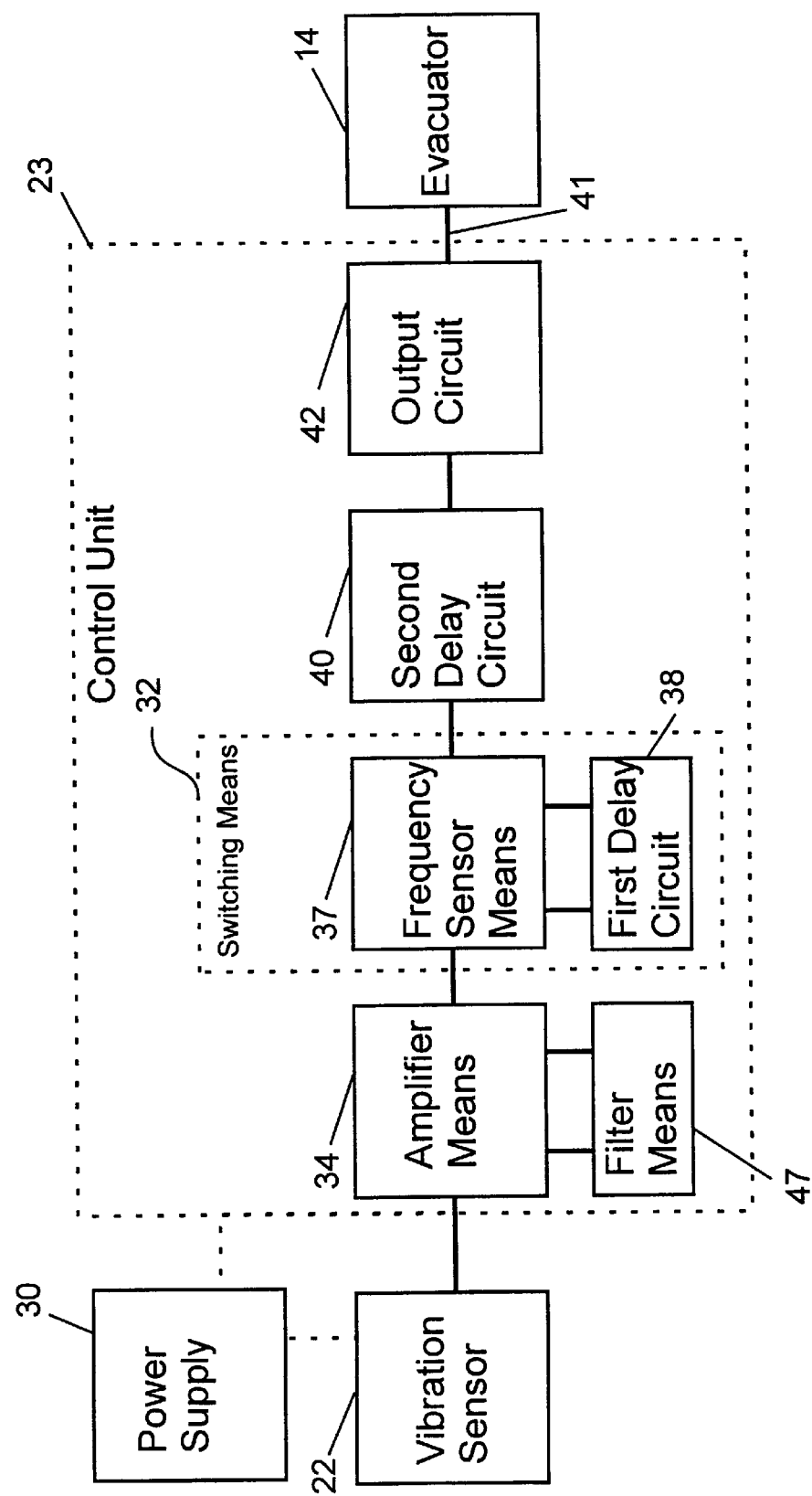
FIG. 3 is a block diagram of the control unit of the switch apparatus illustrated in FIG. 1.

As stated earlier, control unit 23 is in the form of an electronic circuit board assembly. FIG. 3 depicts a block diagram showing the operative relationship of control unit 23, vibration sensor 22 and evacuator 14. Power supply 30 provides power to vibration sensor 22 and control unit 23. Vibration sensor 22 senses many different vibrations throughout a wide band of frequencies and converts these vibrations into an electrical signal which is then conducted to an amplifier means 34. Amplifier means 34 amplifies the magnitude of the current produced by vibration sensor 22. Filter means 47 filters extraneous frequencies not corresponding to those frequencies emitted by speaker 10. In the preferred embodiment, amplifier means 34 provides a gain of approximately 34:1. Amplifier 34 then supplies this amplified signal to switching means 32. Switching means 32 is comprised of frequency sensor means 37 and first delay circuit 38.

First delay circuit 38 is provided to filter extraneous noises common in surgical procedure rooms, such as the beeping of surgical monitors, normal conversations of the surgical staff, and other vibrations not desired to trigger activation of evacuator 14. In addition, first delay circuit 38 provides an operational delay such that extraneous noises containing the frequencies typically generated by speaker 10 do not activate evacuator 14.

Frequency sensor means 37 provides a control signal to second delay circuit 40 when it detects a frequency that approximately matches the frequencies generated by speaker 10. The control signal is routed through second delay circuit 40 and transmitted to output circuit 42. Output circuit 42 directs the control signal 41 to evacuator 14, and the evacuator is turned on. When frequency sensor means 37 no longer detects a frequency approximately corresponding to either the cut or coagulation frequencies of speaker 10, it generates a control signal which turns evacuator 14 off.

Second delay circuit 40 is provided such that a time delay is introduced into the response of the entire system. In this manner, evacuator 14 will continue to operate for a slight period of time subsequent to the termination of operation of the electrosurgical unit 39. This is done so that any remaining plume of toxic smoke generated by electrosurgical unit 39 will continue to be evacuated through evacuator 14.

Figure 4:
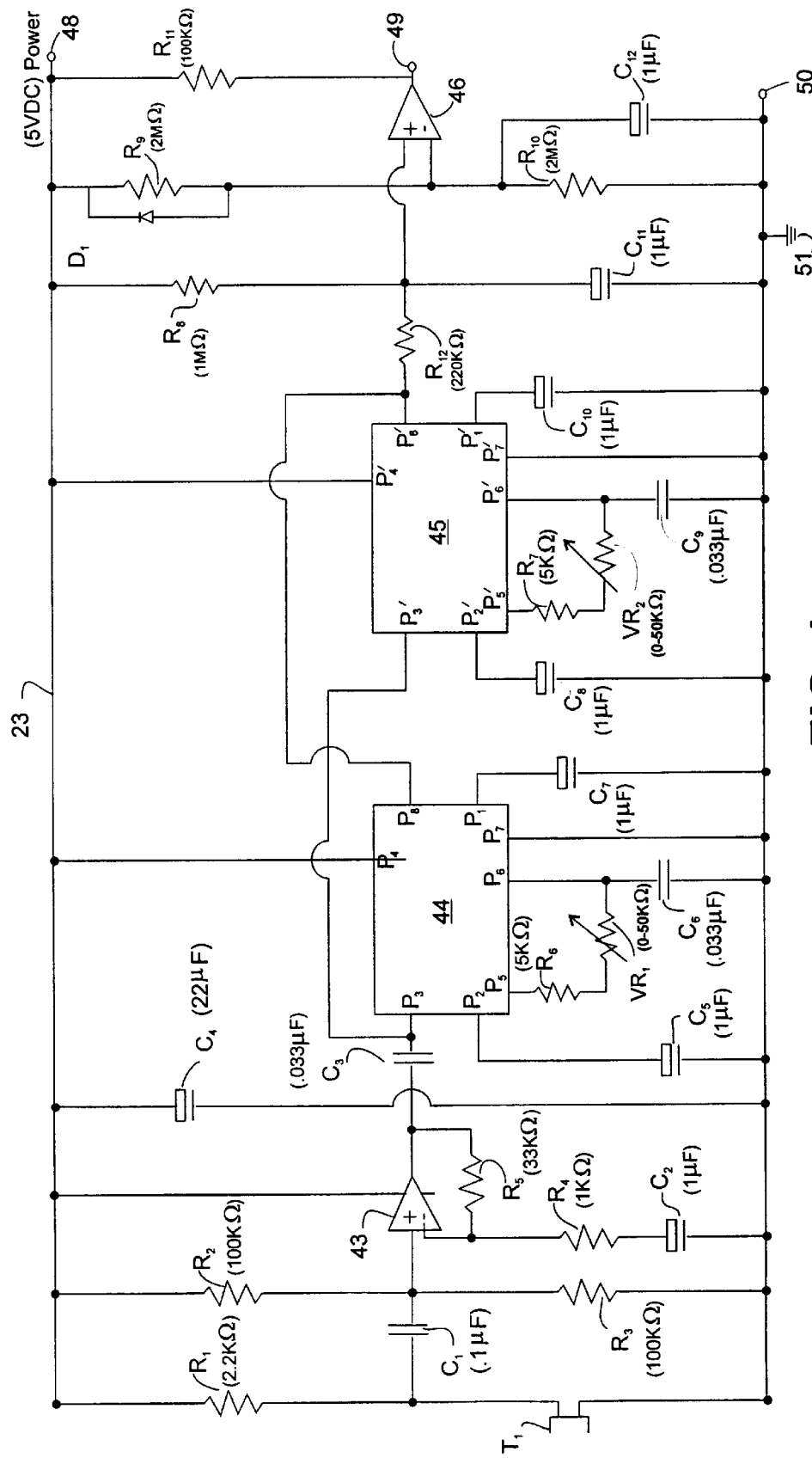
FIG. 4 is an electrical circuit schematic diagram of the block diagram illustrated in FIG. 3.

A preferred embodiment of control unit 23 is illustrated in greater detail in the schematic of FIG. 4. FIG. 4 generally depicts an upper power bus 48 supplying power at 5 Volts DC, a ground bus 50 connected to ground 51 and a control signal node 49. In general, the circuit is comprised of a plurality of resistors $R_1-R_{12}$, a plurality of capacitors $C_1-C_{12}$, variable resistors $VR_1$, $VR_2$, operational amplifier 43, integrated circuits 44, 45, comparator 46, and diode $D_1$. These components are arranged in functional relation, and have the values set forth in FIG. 4 to achieve the functionality of the block diagram of FIG. 3. In this circuit, resistor $R_1$ is mounted in series with vibration sensor $T_1$ between power bus 48 and ground 50. A bipolar capacitor $C_1$ is located at the connection node between transducer $T_1$ and resistor $R_1$. Capacitor $C_1$ serves as a DC blocking capacitor. Resistor $R_1$ acts as a bias resistor and is intended to provide power to transducer $T_1$. Resistors $R_2$ and $R_3$ are positioned in series between power bus 48 and ground 50. Resistors $R_2$ and $R_3$ are amplifier bias resistors intended bias the voltage provided to operational amplifier 43 to around 2.5 V. Resistors $R_4$ and $R_5$ are the gain setting resistors for operational amplifier 43. In the preferred embodiment, the selection of the values for resistor $R_4$ and resistor $R_5$ achieve a gain of approximately 34.

It is noted that operational amplifier 43 is also directly connected with power bus 48. Capacitor $C_2$ is positioned in series with resistor $R_4$ and connected to ground 50. Capacitor $C_3$ is positioned in series between integrated circuit 44 and operational amplifier 43. Capacitors $C_2$, $C_3$ are DC blocking capacitors. In addition, these capacitors serve as filter means 47 and act to filter out certain extraneous frequencies sensed by transducer $T_1$. Operational amplifier 43, resistors $R_5$ and $R_4$ serve as amplifier means 34 for the signal generated by transducer $T_1$.

Integrated circuits 44, 45 are frequency decoder type integrated circuits. In the embodiment shown, integrated circuits 44, 45 are LMC 567CN ICs produced by National Semiconductor Corporation. Integrated circuits 44, 45 each contains pins 1 through 8 (labelled on FIG. 4 as $P_1-P_8$ and $P'_1-P'_8$, respectively). Such integrated circuits are able to recognize an input frequency and then switch the output of pin 8 to accordingly provide a control signal. Output from operational amplifier 43 is connected in parallel to pins 3, 3' of both integrated circuits 44 and 45. Pins 4, 4' of both integrated circuits 44, 45 are connected to the power bus 48. Pin 7, 7' of both integrated circuits 44, 45 are connected to ground 50. Pins 8, 8' of integrated circuits 44, 45 serve as the output pins for each integrated circuit.

Integrated circuit 44, resistor $R_6$, variable resistor $VR_1$, capacitor $C_5$, capacitor $C_6$, and capacitor $C_7$ generally define switching means 32. Based on the output of transducer $T_1$, the output of pin 8 of integrated circuit 44 is switched to produce a control signal 41. Switching means 32 may be further broken down into a frequency sensor means 37 and first delay circuit 38.

The range of frequencies detected is controlled by resistor $R_6$ and variable resistor $VR_1$. This range is typically from 200 $H_z$ to 2.1 $KH_z$. Variable resistor $VR_1$ represents potentiometer 31 depicted in FIG. 1. Hence, integrated circuit 44, resistor $R_6$, capacitor $C_6$ and variable resistor $VR_1$ serve as frequency sensor means 37 to detect frequencies at pin 3 and switch the output of pin 8 when a certain frequency is detected. Capacitor $C_6$ serves as a frequency setting capacitor. The capacitance value of this capacitor effects the frequencies detected by integrated circuit 44.

Capacitors $C_5$ and $C_7$ are delay capacitors. In operation, capacitors $C_5$ and $C_7$ function as first delay circuit 38 shown in FIG. 3. Their use is desirable in that they allow various extraneous vibrations to be filtered out from the operation of integrated circuit 44 by providing a delay period. In practice, their use enables the control unit to either activate or deactivate evacuator 14 in response to the vibrations generated by speaker 10. In addition, they prevent the activation of evacuator 14 on account of extraneous noise such as voices, and other clutter arising in the operating room.

It is noted that the circuitry provided by integrated circuit 45 and the associated capacitors and resistors are analogous to that of integrated circuit 44. This is because integrated circuits 44 and 45 are functionally identical, but are each intended to detect different frequencies. Integrated circuit 44 is intended to provide a control signal to pin 8 upon detection of a frequency corresponding to the frequency emitted from speaker 10 when the cut button 35 of ESU pen 13 is depressed. Integrated circuit 45 is intended to detect the frequency emitted by speaker 10 when the coagulation button 36 is depressed.

Capacitor $C_4$ is an electrolytic-type capacitor which spans power bus 48 and ground 50. This capacitor is intended to serve as a power supply reservoir to ensure power to the control unit in the event that power is momentarily interrupted to bus 48.

The output from pins 8, 8' of integrated circuits 44, 45 is next directed through resistor $R_{12}$. Resistor $R_{12}$ is a delay resistor. This resistor accommodates situations where amplifier 43 becomes saturated. This minimizes false triggering and shut off of the evacuator due to saturation of amplifier 43. Such saturation might occur in the event of great vibration or noise in the proximity of transducer $T_1$.

Resistor $R_8$ and capacitor $C_{11}$ are provided in series between power bus 48 and ground 50. Resistor $R_8$ works in operative relationship with capacitor $C_{11}$ to function as second delay circuit 40. These components cause the output from pins 8, 8' of integrated circuits 44, 45 to be delayed momentarily. In practice, this allows the electrosurgical unit 39 to be deactivated while allowing evacuator 14 to run for some subsequent period of time. This value may be adjusted by adjusting the values of resistor $R_8$ and capacitor $C_{11}$.

Resistors $R_9$, $R_{10}$, $R_{11}$, capacitor $C_{12}$, and comparator 46 represent output circuit 42 shown in FIG. 3. Resistors $R_9$ and $R_{10}$ are provided in series between power bus 48 and ground 50. These resistors are intended to bias the input to comparator 46 to around 2.5 V. A diode $D_1$ is provided in parallel with resistor $R_9$ to discharge capacitor $C_{12}$ on power down of the control unit.

Comparator 46 is necessary to implement the delay strategy of capacitors $C_{11}$ and $R_8$. The output of comparator 46 is in the form of control signal 41 directed to node 49. Resistor $R_{11}$ is located between node 49 and power bus 48 and serves to pull up the voltage of the control signal at node 49. Control signal 41 is typically switched between values of approximately 0 V and 5 V to activate or deactivate the evacuator.

In operation, node 49 provides control signal 41 to evacuator 14. When integrated circuits 44, 45 sense a frequency matching that emitted by speaker 10, a control signal is generated at node 49 and the evacuator 14 is turned on. When integrated circuits 44, 45 no longer sense a frequency matching that emitted by speaker 10, a control signal is generated at node 49 and the evacuator 14 is turned off.

Figure 5:
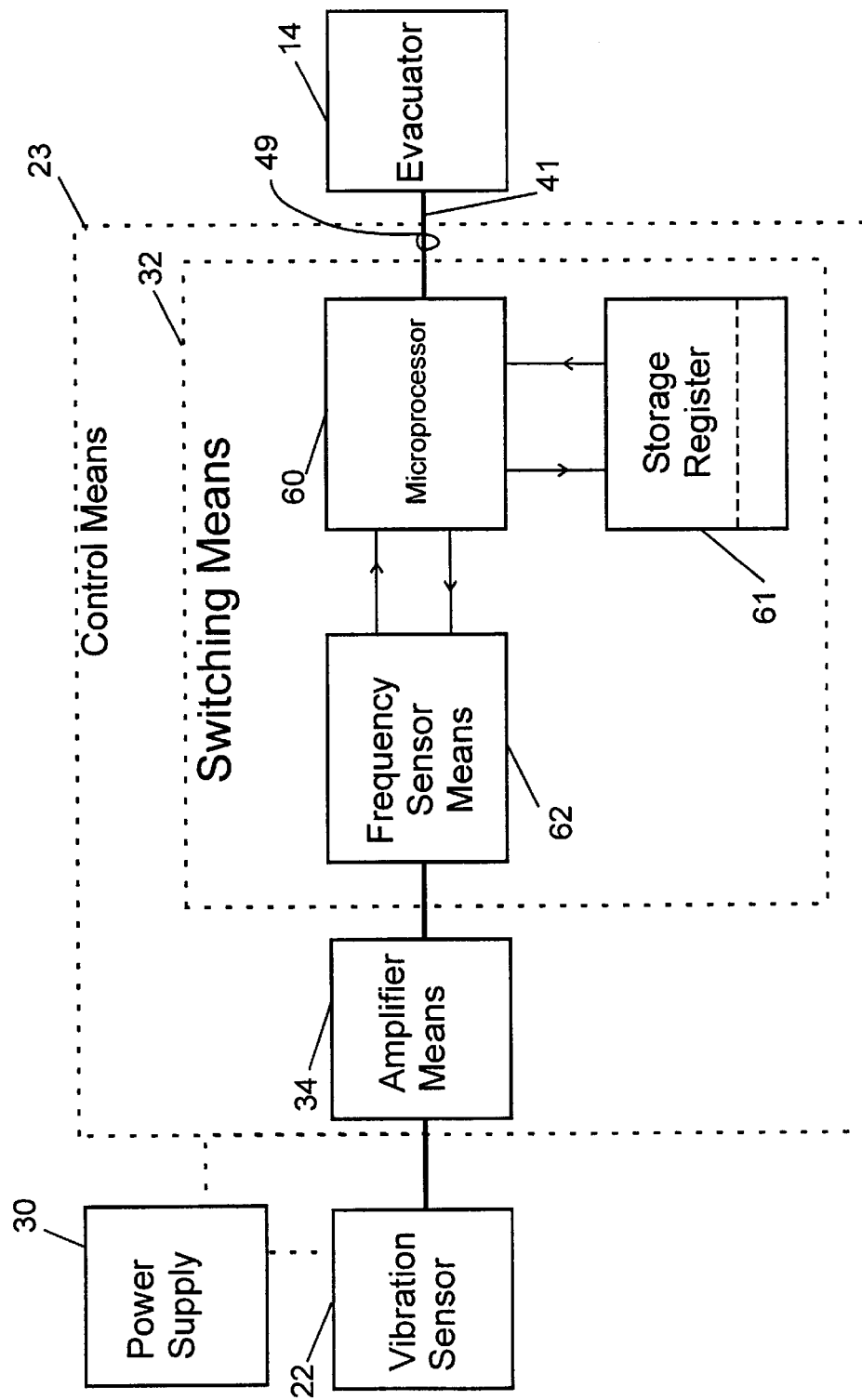
FIG. 5 is a block diagram of an alternate embodiment of the control unit of the switch apparatus illustrated in FIG. 1.

An alternate embodiment of control unit 23 is shown in the block diagram of FIG. 5. Here, a microprocessor 60 is added to the circuit of control unit 23. Control unit 23 operates in essentially the same fashion. Frequency sensor means 62 is now used to feed input into microprocessor 60. In this embodiment, variable resistors $VR_1$ and $VR_2$ are replaced with microprocessor 60 having a number of storage registers 61. Microprocessor 60 has a "learn mode". In this "learn mode", a tone is provided for a predetermined amount of time at a given frequency. The frequency of this tone is sensed by frequency sensor means 62 and transmitted to microprocessor 60. Microprocessor 60 then stores the value of such frequency in one of the nonvolatile storage registers 61. This may be done for a number of frequencies such that a different frequency is stored in each of the registers 61.

Microprocessor 60 may be programmed such that it automatically enters into a "learn mode" after sensing the same frequency for a predetermined period of time. Using a programming language, a number of different schemes could be devised for sampling frequencies and saving them during this learn mode. Alternatively, the microprocessor could be set in a "learn mode" by the manual activation of a switch (not shown). The switch could be turned on to activate the "learn mode", a frequency could be saved in the storage register after it has been sensed for a predetermined period of time, and the switch could then be turned off. This process could be repeated to save a number of frequencies.

After a plurality of values are stored in registers 61 of microprocessor 60 using "learn mode", the control unit 23 is placed in "operating mode". This could occur either automatically after microprocessor 62 has completed an automatic "learn" cycle or manually through the use of a switch. During operating mode, microprocessor 60 provides a signal to frequency sensor 62 which alternates between the number of frequencies stored in the registers of the microprocessor. When a frequency provided by amplifier 34 is matched with one of the frequencies stored in registers 61, microprocessor 60 provides a control signal to node 49 such that evacuator 14 is turned on. When such frequency is no longer sensed by frequency sensor means 62, microprocessor 60 sends a control signal to node 49 such that evacuator 14 is turned off. This embodiment does not require variable resistors to tune the frequency sensors of the control unit. In addition, in this embodiment, a number of frequencies may be detected and stored in the registers. The embodiment of FIG. 4 is only capable of detecting two distinct frequencies. Microprocessor 60 can also perform a delay function, thereby making the separate second delay circuit 40 shown in FIG. 3 unnecessary.

Modifications

The present invention contemplates that many modifications may be made. The particular materials of which the various body parts and components are formed are not deemed critical, and may be readily varied. Further, the various parts and components may take the form shown, or may have some other form, as desired. In addition, while a particular embodiment of the control unit is shown in FIG. 3 as a block diagram, numerous variations of this block diagram may be envisioned whereby the evacuator is controlled in response to the detection of vibrations produced in connection with operation of the surgical device.

In addition, the particular elements set forth in the block diagrams of FIG. 3 and FIG. 5 may take different forms so long as they perform a similar function. For instance, the amplifier means might be incorporated with the vibration sensor. In these contexts, one could easily understand that the control unit may take a number of different variations and forms.

Similarly, the particular electronic circuit depicted in FIG. 4 might easily take a number of different configurations. The particular configuration of FIG. 4 may be varied by any person having ordinary skill in the art. In addition, the inclusion of only two frequency detectors 44, 45 is not meant to be limiting of the instant invention. One skilled in the art could easily modify the circuit of FIG. 4 to detect more or less than two frequencies by the addition or subtraction of integrated circuits similar to integrated circuits 44, 45.

In addition, one skilled in the art may easily determine a number of methods for implementing a "learn mode". Automatic learn modes could be envisioned which rely on a number of frequency sampling techniques or programming methods for programming the microprocessor. A variety of manual learn modes could also be incorporated into the instant invention. Moreover, the particular placement of sensor 22 on the power unit is not critical to a switch apparatus 6 having a learn mode. The sensor 22 could be mounted at a number of places throughout the interior or exterior of the power unit.

In addition, while the preferred embodiment depicts the use of an ESU having two control button 35, 36, it should be understood that the present invention may be used with any other surgical device having any number of operating modes. For instance, in the use of particular lasers, only a single vibrational frequency may be generated. The present invention broadly encompasses detecting such singular frequencies. In addition, other surgical devices may be provided with more than two operating modes. For instance, certain ESUs have three operating modes: one for cutting, one for coagulation, and one for argon. Based on these three operating modes, the vibration sensor will generate three corresponding frequencies. The present invention broadly encompasses such an ESU, and encompasses all surgical devices having any number of operating states corresponding to any number of frequencies generated by a vibration generator.

In addition, the particular mounting configuration shown in FIG. 2 could easily be modified. One skilled in the art could easily envision a number of different mounting arrangements to sense the vibrations generated by speaker 10. For instance, the switch apparatus 6 could be mounted in various locations on the exterior or interior of the power unit 12. Switch apparatus 6 might also be mounted directly to circuit boards already present in the interior of power unit 12 and the electronic circuitry of control unit 23 could be incorporated with such preexisting circuit boards. While a resilient mounting is disclosed, other mountings could easily be provided. While a resilient material is discussed for base 25, other materials might be used. For instance, foam materials, solid materials and other similar materials, resilient or nonresilient may be used. For instance, in the situation where the surgical device is a laser, a more rigid material might be provided. In other situations, the base 25 might be removed entirely to maximize the vibration transmission to sensor 22.

Switch apparatus 6 is shown connected to evacuator 14 by cable 24. Switch 6 might also be in communication with evacuator 14 by other methods such as photoptic, radio transmission or other communication techniques well known to those skilled in the art. In addition, switch apparatus 6 need not draw power via cable 24 because it might be battery operated.

The potentiometers 31, 33 are shown in the preferred embodiment as being manually adjustable. The present invention also covers other tuning means which may be automatically as well as manually adjusted.

The present invention may be used any number of surgical devices. While the preferred embodiment is directed toward the use of an ESU, the present invention may be used with all forms of surgical devices with which vibration is associated. The present invention may be used with surgical lasers, ultrasonic units, argon beam coagulators, surgical drills, surgical saws, surgical reamers, any other form of surgical power tool, endoscopic and laparoscopic tools, tools for use in open procedures, or any other tool to assist a surgeon in minimal evasive and evasive procedures which generate waste products during use.

In addition, the present invention contemplates use with any form of surgical evacuator for the evacuation of fluids. This would include the evacuation of gasborne, airborne, liquidborne or other fluidborne waste products.

The present invention also contemplates numerous vibration sources. While a speaker is shown, any other number of vibration sources are covered by the present invention. Other vibration generation sources include the shutter of a surgical laser, the vibrations caused directly by the power supply of the surgical device, any power unit associated with the surgical unit, the handpiece of a surgical device, and any other vibration sources which are caused in connection with the operation of a surgical device. The vibrations could be measured by the switch apparatus in any number of locations. The vibrations could be measured from the power unit of a surgical device, from the handpiece of the surgical device, from the connecting hardware of the surgical device, from a table upon which the power unit rests or from any other location where sufficient vibrations exist to operate the switch apparatus.

The power unit of the surgical device could take many forms. The power until could be an enclosed electrical power supply in the case of an ESU or laser, or it could be in the form of a pneumatic or hydraulic power supply in the case of certain surgical drills, saws and power tools.

Therefore, while the presently-preferred form of the switch apparatus has been shown and described, and several modifications thereof discussed, persons skilled in this art will readily appreciate that various additional changes and modifications may be made without departing from the spirit of the invention, as defined and differentiated by the following claims.

What is claimed is:

1. A surgical apparatus, comprising:

a surgical laser;

a vibration generator for producing vibrations in response to the operation of said surgical laser;

a vibration sensor for sensing vibrations and for generating an output as a function of vibrations sensed;

control means adaptively coupled to said vibration sensor for producing a control signal as a function of the vibrations produced by said vibration generator; and a surgical evacuator for removing a waste product generated by the use of said surgical laser, said evacuator being responsive to said control signal.

2. A surgical apparatus comprising:

a surgical device;

a vibration generator for producing vibrations in response to the operation of said surgical device;

a vibration sensor for sensing vibrations and for generating an output as a function of vibrations sensed;

control means adaptively coupled to said vibration sensor for producing a control signal as a function of the vibrations produced by said vibration generator;

a surgical evacuator for removing a waste product generated by the use of said surgical device, said evacuator being responsive to said control signal;

said surgical device having a power unit;

said vibration generator being coupled to said power unit;

said power unit having a portion so configured and arranged that operation of said vibration generator causes said portion to vibrate;

said vibration sensor and said control means provided within a housing assembly;

said housing assembly being mounted to said portion of said power unit; and wherein said portion is an exterior portion having plurality of transmission slots.

3. A surgical apparatus comprising:

a surgical device, said surgical device having a power unit;

a vibration generator for producing vibrations in response to the operation of said surgical device, said vibration generator coupled to said power unit;

said power unit having a portion so configured and arranged that operation of said vibration generator causes said portion to vibrate;

a vibration sensor for sensing vibrations and for generating an output as a function of vibrations sensed;

control means adaptively coupled to said vibration sensor for producing a control signal as a function of the vibrations produced by said vibration generator;

said vibration sensor and said control means provided within a housing assembly;

said housing assembly being mounted to said portion of said power unit;

said housing assembly comprising an enclosure and a base, wherein said base is comprised of a resilient material having a first surface and a second surface, said first surface fixedly connected to said portion of said power unit and said second surface fixedly connected to said enclosure; and a surgical evacuator for removing a waste product generated by the use of said surgical device, said evacuator being responsive to said control signal.

4. An apparatus as set forth in claim 3 wherein said resilient material comprises an ethylene propylene diene monomer (EPDM).

* * * * *